(12) United States Patent
Plumptre

(10) Patent No.: US 8,795,239 B2
(45) Date of Patent: *Aug. 5, 2014

(54) BIASING MECHANISM FOR A DRUG DELIVERY DEVICE

(75) Inventor: David Plumptre, Droitwich Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 126 days.

This patent is subject to a terminal disclaimer.

(21) Appl. No.: 13/320,636

(22) PCT Filed: May 28, 2010

(86) PCT No.: PCT/EP2010/057479
§ 371 (c)(1),
(2), (4) Date: Mar. 12, 2012

(87) PCT Pub. No.: WO2010/139635
PCT Pub. Date: Dec. 9, 2010

(65) Prior Publication Data
US 2012/0157930 A1    Jun. 21, 2012

Related U.S. Application Data

(60) Provisional application No. 61/182,825, filed on Jun. 1, 2009.

(30) Foreign Application Priority Data

Jul. 10, 2009 (EP) ..................................... 09009051

(51) Int. Cl.
  *A61M 5/00*    (2006.01)
(52) U.S. Cl.
  USPC ........................................................ 604/232

(58) Field of Classification Search
  USPC ................. 604/187, 207, 214, 218, 232–235; 267/158, 166
  See application file for complete search history.

(56) References Cited

U.S. PATENT DOCUMENTS 2,118,221 A * 5/1938 Montuori ....................... 604/235
5,308,340 A * 5/1994 Harris ............................ 604/208
5,891,106 A * 4/1999 Butuzov et al. ................ 604/209

(Continued)

FOREIGN PATENT DOCUMENTS

DE    9301334    4/1993
EP    0897728    2/1999

OTHER PUBLICATIONS

European Search Report for EP Application No. 09009051, dated Jun. 21, 2010.

(Continued)

*Primary Examiner* — Andrew Gilbert
(74) *Attorney, Agent, or Firm* — McDonnell Boehnen Hulbert & Berghoff LLP

(57) ABSTRACT

The invention refers to a method and an element for biasing a cartridge in a drug delivery device. The element for biasing the cartridge in a cartridge housing of a drug delivery device and an according system comprising the element and the drug delivery device are provided which is a self retained element comprising a first member having a shape that allows passage of a spindle of the drug delivery device. The self retained element biases the cartridge against an inner surface of the cartridge housing. This cartridge could be a removable cartridge.

15 Claims, 4 Drawing Sheets

(56) References Cited

U.S. PATENT DOCUMENTS

| | | | | |
|---|---|---|---|---|
| 6,248,094 | B1* | 6/2001 | Epperson | 604/195 |
| 2002/0052595 | A1* | 5/2002 | Witt et al. | 606/1 |
| 2002/0055734 | A1* | 5/2002 | Houzego et al. | 604/891.1 |
| 2005/0137571 | A1 | 6/2005 | Hommann | |
| 2007/0021718 | A1* | 1/2007 | Burren et al. | 604/110 |
| 2008/0082082 | A1* | 4/2008 | Carlyon et al. | 604/523 |
| 2009/0171298 | A1* | 7/2009 | Magne | 604/232 |
| 2010/0324497 | A1* | 12/2010 | Plumptre | 604/207 |

OTHER PUBLICATIONS

International Search Report and Written Opinion for International App. No. PCT/EP2010/057479, completed Sep. 10, 2010.
"Standard Compression Springs Save Space," Machine Design, Penton Media, Cleveland, Oh, US, vol. 65, No. 11, Jun. 11, 1993, p. 36, XP000374732.

* cited by examiner

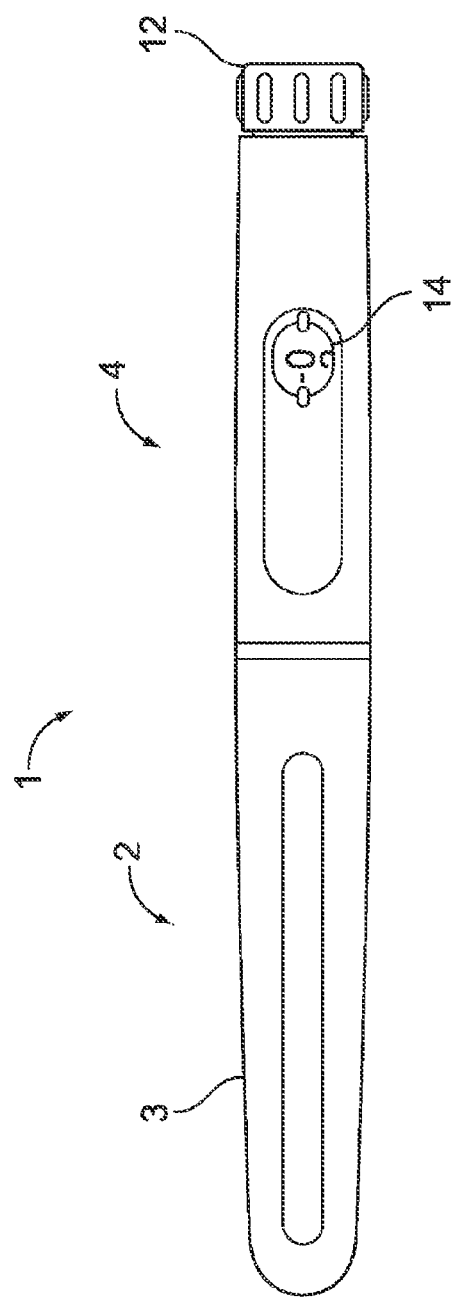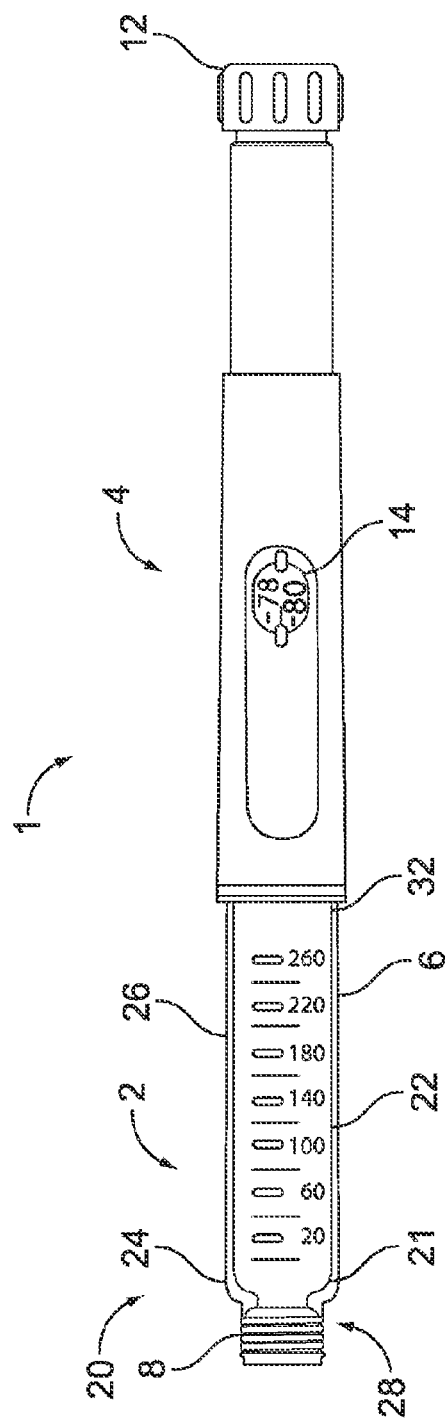

BIASING MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/057479 filed May 28, 2010, which claims priority to U.S. Provisional Patent Application No. 61/182,825 filed on Jun. 1, 2009 and European Patent Application No. 090009051.5 filed on Jul. 10, 2009. The entire disclosure contents of these applications are herewith incorporated by reference into the present application.

FIELD OF THE INVENTION

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. It is therefore important that the distal end of the spindle does not press on the bung except during normal dose dispense, otherwise some loss of drug may be experienced and the subsequent dose would be below the set value.

One perceived disadvantage of certain known medication delivery devices is that because of the various tolerance differences that may occur during manufacturing (e.g., tolerance differences that may arise during component molding) of the various parts making up the drug delivery device, the combination of these various tolerance differences result in that the cartridge may or may not be held rigidly within the cartridge holder. In other words, the cartridge (and hence cartridge bung) may move away relative to the distal end of the spindle. Therefore, there may be times where the cartridge is not held rigidly within the cartridge holder and can therefore move away from an inner front surface of the cartridge holder.

In addition, a needle assembly must frequently be attached to and removed from the cartridge holder. This allows a double ended needle of the needle assembly to pierce the seal of the cartridge. Frequently attaching and re-attaching needle assemblies may cause the cartridge to move within the cartridge holder.

One advantage of certain typical pen type drug delivery devices is that they are relatively compact. This allows a user to carry around the pen. However, if a user of such pen type delivery devices were to drop or mishandle the device, again movement of the cartridge away from the most distal portion of the cartridge holder could result.

There is, therefore, a general need to take these various perceived issues into consideration when designing either resettable or non-resettable pen type drug delivery devices. Such drug delivery devices would help to prevent unwanted movement of a cartridge contained within a cartridge holder. Specifically, such drug delivery devices would help prevent the cartridge from moving axially relative to the cartridge holder during use of the pen type delivery device: when a needle assembly is attached or removed, or when a user carries around (or drops the drug delivery device) during normal use. Preventing such unwanted movement of the cartridge within the cartridge holder would tend to help insure dispensing accuracy by the device by preventing the spindle distal end from pressing on the bung of the cartridge.

SUMMARY

It is an object of the present invention to provide an improved drug delivery device with regard to above explained needs.

This object is solved by an element configured for biasing a cartridge in a cartridge housing of a drug delivery device, wherein at least one portion of said element is configured to be self retained by an internal surface of said drug delivery device.

According to an exemplary arrangement, a non-plastic element for biasing a cartridge in a cartridge housing of a drug delivery device is provided. This non-plastic element does not comprise a coil spring. According to another exemplary arrangement, a self retained element for providing a spring bias to a cartridge in a cartridge holder of a drug delivery device comprises a first member having a shape that allows passage of a spindle of the drug delivery device. A portion of the first member is self retained by an internal surface of the drug delivery device. The self retained element biases the cartridge against an inner surface of the cartridge holder. In one arrangement, this cartridge is a removable cartridge. In another exemplary arrangement the element for biasing a cartridge comprises a first member and a second member folded over said first member. In a further exemplary arrangement said element comprises a first dimension associated with an uncompressed state when said element is not biasing said cartridge; and a second dimension associated with a compressed state when said element is biasing said cartridge, such that a difference between said first dimension and said second dimension is less than approximately 4 mm and preferably more than approximately 0.5 mm.

The object is further solved by a system of the element configured for biasing a cartridge described above and a drug delivery device wherein said drug delivery device comprises a cartridge housing containing a cartridge. In an exemplary arrangement said drug delivery device comprises a cartridge housing with a removable cartridge. According to an exemplary arrangement the cartridge housing comprises a needle attaching portion, said needle attaching portion allowing for a mounting of a removable needle assembly.

Further, the object is solved by a method of biasing a cartridge in a drug delivery device cartridge holder is provided. The method comprises the steps of defining an inner end face and a first inner surface of a cartridge holder housing and positioning a cartridge along the first inner surface of the cartridge housing. The method also includes the steps of positioning a self retained biasing element in a dose setting mechanism, preferably by flexibly engaging said self retained biasing element within the housing of said dose setting mechanism, and connecting the dose setting mechanism to the cartridge housing. According to an exemplary arrangement the self retained biasing element is manufactured as a unitary element. According to another exemplary arrangement the self retained biasing element is compressed to a compressed height of less than approximately 4 mm and preferably more than approximately 0.5 mm.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates an arrangement of the drug delivery device in accordance with the one aspect of the present invention;

FIG. 2 illustrates the drug delivery device of FIG. 1 with a cap removed and showing a cartridge holder containing a biased cartridge;

DETAILED DESCRIPTION

Figure 3:
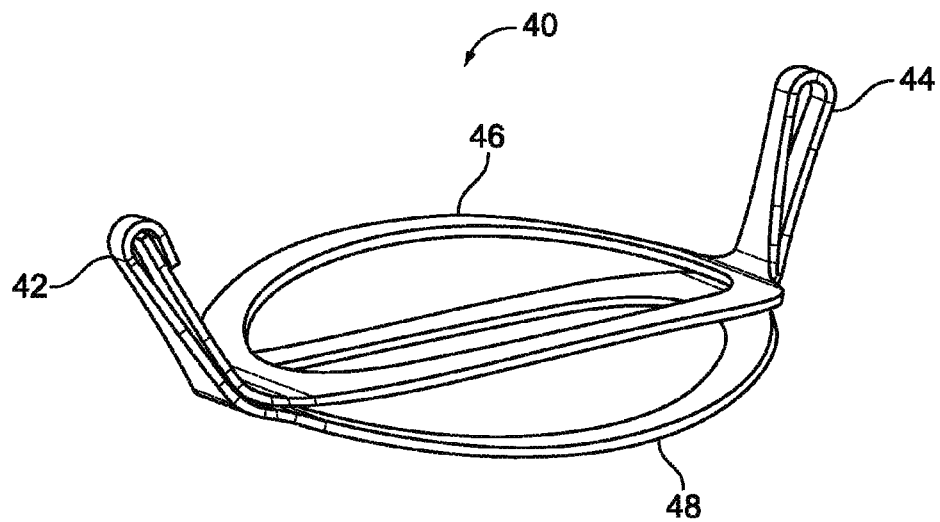
FIG. 3 illustrates a perspective view of a biasing element that may be used to bias the cartridge contained in the cartridge holder of the drug delivery device illustrated in FIG. 2.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38[Asp28] Exendin-4(1-39)-NH2,
H-Asn-(Glu)5des Pro36, Pro37, Pro38[Asp28] Exendin-4(1-39)-NH2,
des Pro36, Pro37, Pro38[Asp28] Exendin-4(1-39)-(Lys)6-NH2,
H-(Lys)6-des Pro36, Pro37, Pro38[Asp28] Exendin-4(1-39)-(Lys)6-NH2, H-Asn-(Glu)5-des Pro36, Pro37, Pro38[Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38[Trp(O2)25] Exendin-4(1-39)-NH2,
H-(Lys)6-des Pro36, Pro37, Pro38[Trp(O2)25, Asp28] Exendin-4(1-39)-NH2,
H-Asn-(Glu)5-des Pro36, Pro37, Pro38[Trp(O2)25, Asp28] Exendin-4(1-39)-NH2,
des Pro36, Pro37, Pro38[Trp(O2)25, Asp28] Exendin-4(1-39)-(Lys)6-NH2,
H-(Lys)6-des Pro36, Pro37, Pro38[Trp(O2)25, Asp28] Exendin-4(1-39)-(Lys)6-NH2,
H-Asn-(Glu)5-des Pro36, Pro37, Pro38[Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38[Met(O)14, Asp28] Exendin-4(1-39)-NH2,
H-Asn-(Glu)5-des Pro36, Pro37, Pro38[Met(O)14, Asp28] Exendin-4(1-39)-NH2,
des Pro36, Pro37, Pro38[Met(O)14, Asp28] Exendin-4(1-39)-(Lys)6-NH2,
H-(Lys)6-des Pro36, Pro37, Pro38[Met(O)14, Asp28] Exendin-4(1-39)-(Lys)6-NH2,
H-Asn-(Glu)5 des Pro36, Pro37, Pro38[Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38[Met(O)14, Trp(O2)25] Exendin-4(1-39)-NH2,
H-(Lys)6-des Pro36, Pro37, Pro38[Met(O)14, Asp28] Exendin-4(1-39)-NH2,
H-Asn-(Glu)5-des Pro36, Pro37, Pro38[Met(O)14, Trp(O2) 25, Asp28] Exendin-4(1-39)-NH2,
des Pro36, Pro37, Pro38[Met(O)14, Trp(O2)25, Asp28] Exendin-4(1-39)-(Lys)6-NH2,
H-(Lys)6-des Pro36, Pro37, Pro38[Met(O)14, Trp(O2)25, Asp28] Exendin-4(S1-39)-(Lys)6-NH2,
H-Asn-(Glu)5-des Pro36, Pro37, Pro38[Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with a first arrangement of the present invention. The drug delivery device 1 comprises a housing having a first cartridge retaining part 2, and dose setting mechanism 4. The drug delivery device may be a non-resettable drug delivery device (i.e., a non-reusable device) or alternatively a resettable drug delivery device (i.e., a reusable device). A first end of the cartridge retaining means 2 and a second end of the dose setting mechanism 4 are secured together by connecting features. For non-resettable devices, these connecting features would be permanent and for resettable devices, these connecting features would be releasable.

In this illustrated arrangement, the cartridge retaining means 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialled dose will become viewable in the window or lens 14 by way of the dose scale arrangement.

FIG. 2 illustrates the medical delivery device 1 of FIG. 1 with the cover 3 removed from a distal end 20 of the medical delivery device 1. This exposes the cartridge housing 6 (cartridge holder). As illustrated, a cartridge 22 from which a number of doses of a medicinal product may be dispensed, is provided in the cartridge housing 6. Preferably, the cartridge 22 contains a type of medicament that must be administered relatively often, such as once or more times a day. One such medicament is either long acting or short acting insulin or an insulin analog. The cartridge 22 comprises a bung or stopper (not illustrated in FIG. 2) that is retained near a second end or a proximal end 32 of the cartridge 22.

The cartridge housing 6 has a distal end 24 and a proximal end 26. Preferably, the distal end 24 of the cartridge housing 6 comprises a groove 8 for attaching a removable needle assembly however other needle assembly connection mechanisms could also be used. If the drug delivery device 1 comprises a resettable device, the cartridge housing proximal end 26 is removably connected to the dose setting mechanism 4. In one preferred embodiment, cartridge housing proximal end 26 is removably connected to the dose setting mechanism 4, preferably to an inner or an outer housing of the dose setting mechanism 4, via a bayonet connection. However, as those of ordinary skill in the art will recognize, other types of removable connection methods such as threads, partial threads, ramps and detents, snap locks, snap fits, and luer locks may also be used.

The cartridge housing 6 further comprises an inner end face 28 near the first end or distal end 24 of the cartridge housing 6. Preferably, in order to maintain dose accuracy, the cartridge 22 is pressed up against or abuts this inner end face 28. In order to achieve this abutment, as will be discussed in greater detail below, the drug delivery device 1 comprises a biasing member 40 (or biasing means, e.g., a non-coiled spring element) that biases the cartridge 22 against this inner end face 28. In one preferred arrangement, this biasing member 40 comprises a self retained spring like member that is releasably connected to an inner or outer housing of the dose setting mechanism 4. By self retained, it is meant that no other component part is required to retain the biasing member 40 to the drug delivery device.

As previously mentioned, the dose setting mechanism 4 of the drug delivery device illustrated in FIG. 2 may be utilized as a reusable drug delivery device. (i.e., a drug delivery device that can be reset). Where the drug delivery device 1 comprises a reusable drug delivery device, the cartridge 22 is removable from the cartridge housing 6. The cartridge 22 may be removed from the device 1 without destroying the device 1 by merely having the user disconnect the dose setting mechanism 4 from the cartridge housing 6.

In use, once the removable cap 3 is removed, a user can attach a suitable needle assembly (not illustrated) to the groove 8 provided at the distal end 24 of the cartridge housing 6. Such needle assembly may be screwed onto a distal end 24 of the housing 6 or alternatively may be snapped onto this distal end 24. After usage, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

FIG. 3 illustrates a perspective view of a biasing member 40 that may be used to bias the cartridge 22 contained in the cartridge housing 6 of the drug delivery device 1 illustrated in FIGS. 1 and 2. In one preferred arrangement, the biasing member 40 is assembled between the cartridge 22 and the dose setting mechanism 4 of a drug delivery device 1. In this position, the biasing member 40 biases the cartridge 22 in an axial direction so that the distal end 21 of the cartridge 22 remains up against the inner end face 28 of the cartridge housing 6.

Using the biasing member 40 between the dose setting mechanism 4 and the cartridge 22 results in certain perceived advantages. First, the biasing member 40 will tend to prevent the cartridge 22 from moving axially relative to the cartridge housing 6 when a needle assembly is connected to or disconnected from the distal end 24 of the cartridge housing 6. Second, the biasing member 40 will also help prevent the cartridge 22 from moving axially relative to the cartridge housing 6 when a user handles the device or inadvertently drops the drug delivery device 1. Third, because of the flexible nature of the biasing member, the biasing member 40 will tend to hold the cartridge 22 adjacent the inner end face 28 of the cartridge housing 6 even where a range of manufacturing tolerances between the various component parts particularly in axial direction is experienced. This will therefore help to ensure dose setting and dose administration accuracy of the drug delivery device 1.

Returning to FIG. 3, preferably, the biasing member 40 comprises a first connection side loop 42 and a second connection side loop 44. These connection side loops 42 and 44 are disposed at opposite ends of the biasing member 40. These side loops 42, 44 are flexible substantially in a direction radial to the longitudinal axis of the cartridge 22 or the cartridge housing 6 and allow the biasing member 40 to be assembled into a distal end of a dose setting mechanism 4, preferably in two side apertures of the inner or outer housing of the dose setting mechanism, and be self retained therein.

The biasing member 40 further comprises an upper wave spring 46 and a lower wave spring 48. Both wave springs 46, 48 have inner diameters and outer diameters that are essentially equal. The upper wave spring 46 and the lower wave spring 48 illustrated in FIG. 3 are shown in an uncompressed or unbiased state. In this state, the upper wave spring 46 is flexing in a proximal direction and the lower wave spring 48 is flexing in a distal direction relative to the connection side loops.

Unlike certain conventional coil springs, when the biasing mechanism 40 is in a biased state or is in a compressed state, the biasing mechanism has a relatively small height H2 (see FIG. 8), in the order of only approximately between 1.9 mm and 0.5 mm. The biasing member 40 has also been designed so that it is self retained in the dose setting mechanism 4 using two small side apertures into which side loops 42, 44 lock when assembled into the dose setting mechanism 4.

Figure 4:
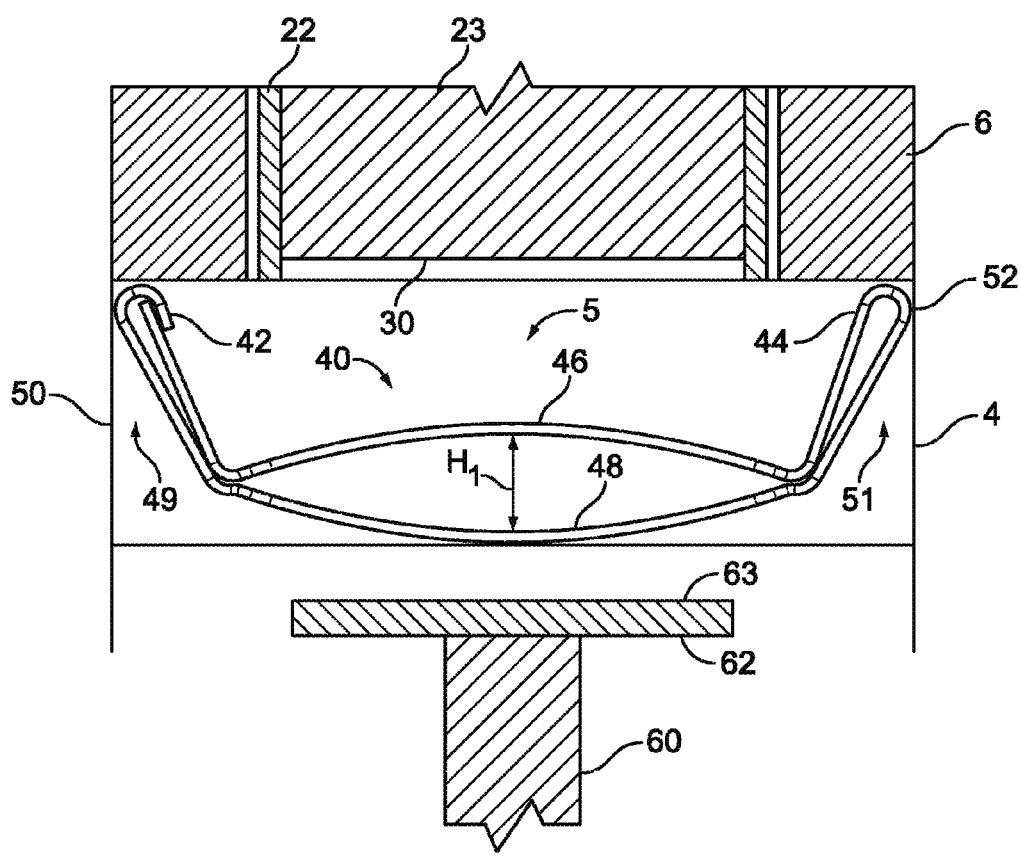
FIG. 4 illustrates one arrangement for mounting the biasing element illustrated in FIG. 3 in a drug delivery device, such as the drug delivery device illustrated in FIGS. 1-2.

FIG. 4 illustrates one arrangement for assembling the biasing member 40 in the drug delivery device 1 illustrated in FIGS. 1-2. As illustrated in FIG. 4, the cartridge housing 6 is shown partially connected to the dose setting mechanism 4 and the biasing member 40 is in an uncompressed state. If the cartridge housing 6 were fully connected to the dose setting mechanism 4, the cartridge 22 would act on the upper wave spring 46 so as to result in both the upper and lower wave springs 46, 48 being in a compressed or biased state (see, e.g., FIG. 8). However, for ease of explanation, FIG. 4 merely illustrates the cartridge housing 6 and the dose setting mechanism in a partially connected position.

When the biasing member 40 is assembled within the dose setting mechanism 4, the first connecting side loop 42 flexes inwards towards an internal cavity 5 of the dose setting mechanism 4. The flexing nature of the first side loop 42 allows the loop 42 to engage a first aperture 49 in a first side wall 50 of the inner or outer housing of the dose setting mechanism 4. Similarly, the second connecting side loop 44 also flexes inwards towards the internal cavity 5 of the dose setting mechanism 4 internal cavity 5. This second connecting side loop 44 engages a second aperture 51 in a second side wall 52 of the inner or outer housing of the dose setting mechanism 4. Preferably, the first side wall 50 and the second side wall 52 may form the same side wall. In this uncompressed or unbiased state of biasing member 40, a difference in height between the upper wave spring 46 and the lower wave spring 48 has been designated in FIG. 4 by H1.

The biasing mechanism 40 can be retained in the housing whose internal diameter is just slightly larger than the outer diameter of the cartridge 22. More preferably, the biasing member 40 can be assembled over a spindle whose maximum outer diameter is slightly less than an inner diameter of the cartridge 22. For example, in FIG. 4, the dose setting mechanism 4 comprises a spindle 60 for acting on a proximal surface 30 of bung 23 of a cartridge 22 so that medicine can be expelled from the cartridge 22. The spindle 60 may comprise a spindle bearing 62 near a distal end of the spindle. The spindle bearing 62 comprises a spindle bearing surface 63 for acting on the proximal surface 30 of the bung 23. The biasing mechanism 40 has an inner diameter that is slightly larger than an outer diameter of the spindle bearing 62 or spindle 60 so that an assembled biasing mechanism 40 does not impede movement of this spindle 60 or the spindle bearing 62 during use of the drug delivery device. (i.e., during dose administration or during drug delivery device reset).

Figure 5:
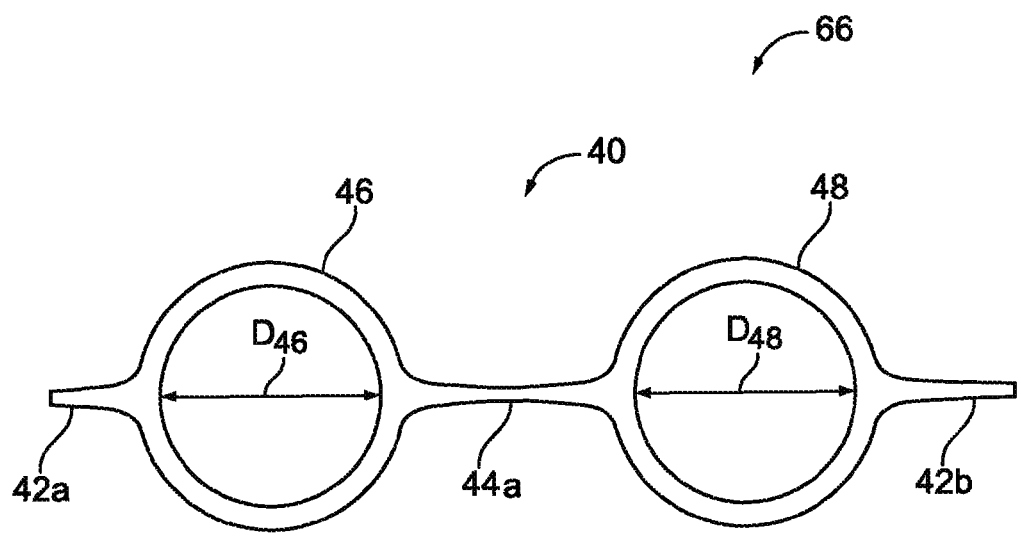
FIG. 5 illustrates a flat profile of the biasing element illustrated in FIG. 3.

FIG. 5 illustrates a flat profile 66 of the biasing mechanism 40 illustrated in FIG. 3. As illustrated in FIG. 5, the biasing member 40 comprises a self-contained part or a single unitary part. This self contained member comprises a first member and a second member that are flexibly coupled to one another. The first member comprises an upper wave spring 46 having an inner diameter designated in FIG. 5 by D46 as well as a bar-like left side section 42a and bar-like right side section 44a. The second member comprises a lower wave spring 48 having an inner diameter designated in FIG. 5 by D48 as well as a bar-like left side section 44a and a bar-like right side section 42b. The flexible nature of the first and second members, in particular of the side sections 42a, 42b, 44a, allow these members to be manipulated or bent or folded over one another to form the biasing mechanism 40 illustrated in FIG. 3. In one preferred arrangement, the upper and lower wave springs 46, 48 comprise circular members however those of skill in the art will recognize other shapes may be utilized as well.

Preferably, once the biasing mechanism 40 is in a folded state, the side section 42a engages the side section 42b to form a first connection side loop 42. Therefore the front end part of side section 42b is bent forming a round section as a brace support for the front end part of the side section 42a which is accommodated behind the front end part of side section 42b (cf. FIG. 3). The side section 44a is bent in the way that it forms a second connection side loop 44. In addition, the inner diameter D46 is generally equal to the inner diameter D48 of the second member. This may be seen from FIG. 6.

Figure 6:
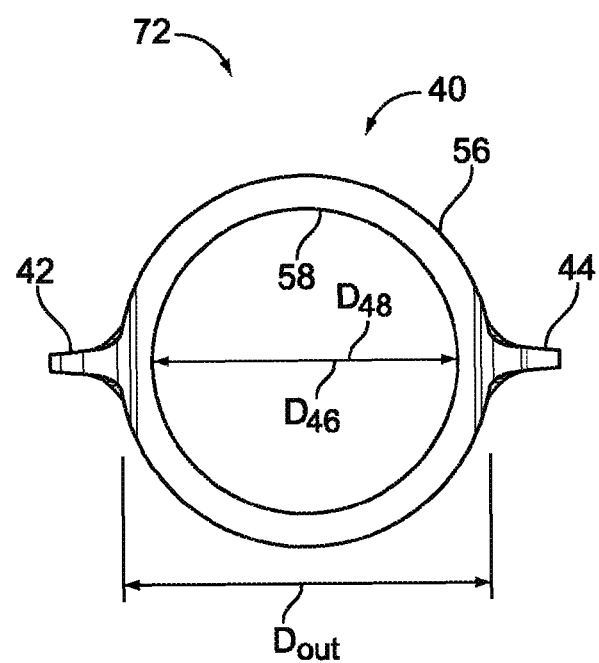
FIG. 6 illustrates a folded profile of the biasing element illustrated in FIG. 5.

FIG. 6 illustrates a folded profile 72 of the biasing member 40 illustrated in FIG. 3. As can be seen from this folded profile 72, when the first member 46 and second member 48 are folded over one another, the biasing member 40 will now have an inner diameter D46, D48 and an outer diameter Dout. Preferably, the inner diameter D46, D48 of the biasing member 40 will be sized to be larger in size or roughly the same size as the inside diameter of the cartridge 22. In addition, the outside diameter 56 identified as Dout of the biasing member 40 will be sized to be smaller or roughly the same size as the outside diameter of the cartridge 22.

Figure 7:
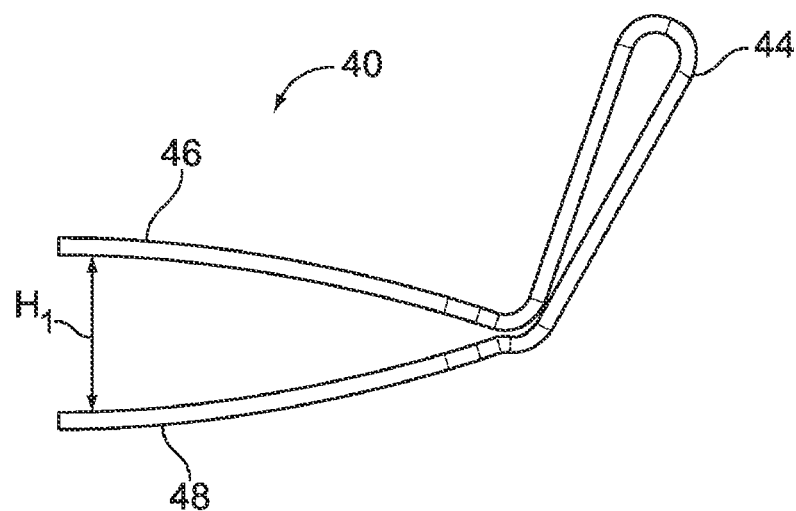
FIG. 7 illustrates one perspective side view of a folded profile of the biasing element illustrated in FIG. 3 in a no load state or an uncompressed state.

FIG. 7 illustrates a partial side view of the folded profile 72 of the biasing member 40 illustrated in FIG. 3. In this partial side view, the biasing member 40 is illustrated in a no load state. That is, where the biasing member 40 is not biasing a cartridge similar to that illustrated in FIG. 4. In this unbiased state, the upper wave spring 46 of the biasing member 40 will have a first dimension associated with an uncompressed state and the lower wave spring 48 will have a first dimension associated with this uncompressed state. The difference in height between these two dimensions is represented by the height H1.

Figure 8:
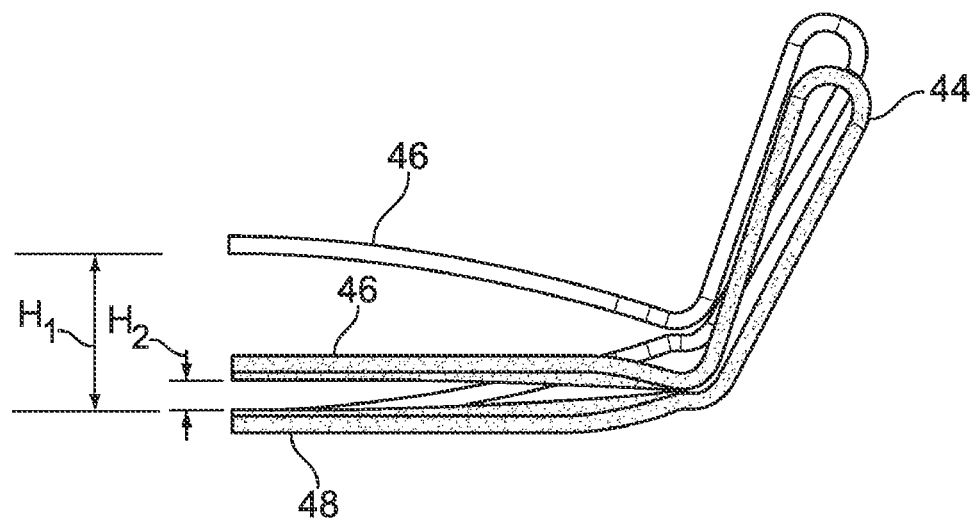
FIG. 8 illustrates one perspective side view of a folded profile of the biasing element illustrated in FIG. 3 in a loaded (or a compressed state) and in a no load state (or in an uncompressed state).

FIG. 8 illustrates a folded profile of the biasing member 40 illustrated in FIG. 3 in a compressed state: where the biasing member 40 is biasing a cartridge, in comparison with the biasing member 40 in the uncompressed state. In this bent state, the upper wave spring 46 of the biasing mechanism will have a second or different dimension than in the uncompressed state. (Cf., FIG. 7). Similarly, the lower wave spring 48 will have a second or different dimension than in the uncompressed state. (Cf., FIG. 7). The difference in height between the upper wave spring 46 and the lower wave spring 48 in this compressed state is represented by the height H2.

In one preferred arrangement, the difference in height between the uncompressed state H1 and the compressed state H2 of the biasing member 40 will be greater than approximately 0.5 mm, and preferably less than approximately 4 mm. One advantage of this arrangement is that this low height H2 allows for having a shorter (and less obtrusive) drug delivery device, an advantage for certain users that must carry their pen type drug delivery devices with them throughout the day.

Exemplary embodiments of the present invention have been described. Those skilled in the art will understand, however, that changes and modifications may be made to these embodiments without departing from the true scope and spirit of the present invention, which is defined by the claims.

The invention claimed is:

1. An element configured for biasing a cartridge in a cartridge housing of a drug delivery device having a longitudinal axis, wherein at least one portion of said element is configured to be self retained by an internal surface of said drug delivery device and wherein said element comprises
   a first member having first and second side sections, where the second side section is connected to a first side section of a second member to form a first connection loop and where the first and second members are oriented such that the first side section of the first member and a second side section of the second member form a second connection loop, where the first and second connection loops are configured to flex in a radial direction relative to the longitudinal axis to engage the internal surface of said drug delivery device for self retention within said drug delivery device.

2. The element of claim 1 further characterized in that
   the second member is folded over said first member,
   said first member having a shape to allow passage of a spindle of said drug delivery device during dose administration of said drug delivery device.

3. The element of claim 1, wherein said element further comprises
   a first dimension defined as a height between the first member and the second member associated with an uncompressed state when said element is not biasing said cartridge; and
   a second dimension being less than the first dimension associated with a compressed state when said element is biasing said cartridge,
   such that a difference between said first dimension and said second dimension is less than approximately 4 mm and more than approximately 0.5 mm.

4. The element of claim 1, wherein said
   first member comprises an upper wave spring, and
   said second member comprises a lower wave spring flexibly coupled to said upper wave spring by said first connection loop.

5. The element of claim 4 wherein said upper wave spring comprises an outer diameter smaller than an outer diameter of said cartridge.

6. The element of claim 4 wherein said upper wave spring comprises an inner diameter greater than an inner diameter of said cartridge.

7. A system comprising,
   an element according to claim 1 and a drug delivery device, wherein said drug delivery device comprises a cartridge housing containing a cartridge which is a removable cartridge.

8. The system of claim 7, wherein said removable cartridge is a cartridge from which a number of doses of a medicinal product may be dispensed.

9. The system of claim 7, wherein said cartridge housing comprises a needle attaching portion, said needle attaching portion allowing for a mounting of a removable needle assembly.

10. The system of claim 9, wherein when a user connects or disconnects the removable needle assembly to or from said needle attaching portion of said cartridge housing, said element prevents said removable cartridge from moving axially relative to said cartridge housing.

11. The system of claim 9, wherein said needle attaching portion comprises a helical groove.

12. A method of biasing a cartridge in a drug delivery device cartridge housing having a longitudinal axis, said method comprising the steps of:
- defining an inner end face and a first inner surface of the drug delivery device cartridge housing;
- positioning a cartridge along said first inner surface of said drug delivery device cartridge housing;
- positioning a self retained biasing element in a dose setting mechanism, wherein said self retained biasing element comprises a first member having first and second side sections, where the second side section is connected to a first side section of a second member to form a first connection loop and where the first and second members are oriented such that the first side section of the first member and a second side section of the second member form a second connection loop, where said first and said second connection loops are configured to flex in a radial direction relative to the longitudinal axis to engage an inner surface of housing of the dose setting mechanism for self retention within a drug delivery device; and
- connecting said dose setting mechanism to the drug delivery device cartridge housing to form the drug delivery device.

13. The method of claim 12 further comprising the step of:
utilizing said self retained biasing element to maintain said cartridge against said inner end face of the drug delivery cartridge housing.

14. The method of claim 12 further comprising the step of: manufacturing said self retained biasing element as a unitary element.

15. The method of claim 12 further comprising the step of: compressing said self retained biasing element to a compressed height of less than approximately 4 mm and more than approximately 0.5 mm.

* * * * *